US008481083B2

(12) United States Patent
Xu et al.

(10) Patent No.: US 8,481,083 B2
(45) Date of Patent: *Jul. 9, 2013

(54) GRANULAR COMPOSITIONS OF MAGNESIUM OXIDE AND CITRIC ACID AND USES THEREOF

(75) Inventors: Haijun Xu, Zhongshan Port (CN); Tiejun Diao, Zhongshan Port (CN)

(73) Assignee: Ferring International Center S.A., St-Prex (CH)

( * ) Notice: Subject to any disclaimer, the term of this patent is extended or adjusted under 35 U.S.C. 154(b) by 0 days.

This patent is subject to a terminal disclaimer.

(21) Appl. No.: 12/677,857

(22) PCT Filed: Oct. 10, 2008

(86) PCT No.: PCT/IB2008/003199
§ 371 (c)(1),
(2), (4) Date: Dec. 15, 2010

(87) PCT Pub. No.: WO2009/047633
PCT Pub. Date: Apr. 16, 2009

(65) Prior Publication Data
US 2011/0104285 A1    May 5, 2011

Related U.S. Application Data

(60) Provisional application No. 60/980,549, filed on Oct. 17, 2007.

(30) Foreign Application Priority Data

Oct. 12, 2007  (EP) .................................. 07254049
Nov. 9, 2007   (CN) .......................... 2007 1 0186023
Apr. 1, 2008   (GB) .................................. 0805953.7

(51) Int. Cl.
| | |
|---|---|
| *A61K 9/16* | (2006.01) |
| *A61K 9/50* | (2006.01) |
| *A61K 9/14* | (2006.01) |
| *A61K 31/33* | (2006.01) |
| *A61K 31/435* | (2006.01) |
| *A01N 43/00* | (2006.01) |
| *A01N 43/40* | (2006.01) |

(52) U.S. Cl.
USPC ............ 424/490; 424/489; 514/183; 514/277

(58) Field of Classification Search
None
See application file for complete search history.

(56) References Cited

U.S. PATENT DOCUMENTS

| 5,045,459 | A | * | 9/1991 | Mothes et al. ................. 435/144 |
| 5,102,682 | A | | 4/1992 | Nasrallah et al. |
| 5,219,598 | A | | 6/1993 | Anderson et al. |
| 5,290,962 | A | * | 3/1994 | Ozdoba et al. ................. 516/109 |
| 5,498,425 | A | | 3/1996 | Wood et al. |
| 5,631,022 | A | | 5/1997 | Mandel et al. |
| 5,674,529 | A | | 10/1997 | Marder et al. |
| 6,514,537 | B1 | | 2/2003 | Murphy |

FOREIGN PATENT DOCUMENTS

| DE | 19962251 A1 | 9/2001 |
| EP | 772977 A3 | 5/1998 |
| EP | 771562 A3 | 11/1998 |
| EP | 1810579 A1 | 7/2007 |
| GB | 1300969 A | 12/1972 |
| WO | WO03074061 A1 | 9/2003 |
| WO | WO2004052289 A2 | 6/2004 |
| WO | WO2009047633 A3 | 9/2009 |

OTHER PUBLICATIONS

PICOLAX SPC, Ferring Pharmaceuticals, Summary of Product Characteristics, Dec. 2003, pp. 1-4.*
Anonymous: "Picolax SPC" Ferrings Product Characteristics, [online] Dec. 2003 m XP002492151 Retrieved from the Internet: URL:www.ferring.co.uk/index.php?option=com.*
Ferring Pharmaceuticals Inc., FDA label for drug product, PICOPREP (Jul. 2012).

* cited by examiner

*Primary Examiner* — Fereydoun G Sajjadi
*Assistant Examiner* — Michael B Pallay
(74) *Attorney, Agent, or Firm* — Fish & Richardson P.C.

(57) ABSTRACT

Compositions are provided that are useful for the preparation of a medicament. The compositions comprise granules having a layer of sodium picosulphate coated on potassium bicarbonate. Additional granules having a layer of magnesium oxide coated on a core of citric acid are also provided. The two types of granules may be combined to obtain mixtures (preferably homogeneous or substantially homogeneous mixtures) of the two types of granules, which are useful, e.g., as pharmaceutical compositions.

11 Claims, No Drawings

GRANULAR COMPOSITIONS OF MAGNESIUM OXIDE AND CITRIC ACID AND USES THEREOF

The present application is the U.S. National Phase of International Patent Application Serial No. PCT/IB2008/003199, filed Oct. 10, 2008, which claims priority to European Patent Application Serial No. 07254049.5, filed Oct. 12, 2007, U.S. Provisional Patent Application Ser. No. 60/980,549, filed Oct. 17, 2007, Chinese Patent Application Serial No. 2007 10 186023.6, filed Sep. 11, 2007, and UK Patent Application Serial No. 0805953.7, filed Apr. 1, 2008. The contents of the foregoing applications are hereby incorporated by reference in their entireties.

The present invention relates to an improved process for the manufacture of a pharmaceutical product, and products and intermediate products resulting therefrom.

BACKGROUND OF THE INVENTION

A pharmaceutical product used for clearance of the bowel prior to X-ray examination, endoscopy or surgery, is presently sold under the trade mark name of PICOLAX™. The pharmaceutical product is a white powder which is made up as a solution (in water) for administration. The properties required are that it is a strong laxative that is easily palatable. The pharmaceutical product includes sodium picosulphate (PS), a stimulant laxative; and anhydrous citric acid (CA) and magnesium oxide (MgO, light), which together in solution form magnesium citrate, an osmotic laxative with a powerful cathartic effect.

The dosage form for oral delivery is in the form of granules. Herein the term granule(s) includes loose particles (such as particles which might collectively be termed a powder, including loose particles in the form of a powder which is known in the art as "powder for oral administration"). The product is a physical mixture of six raw materials; these being citric acid (e.g. citric acid anhydrous or citric acid monohydrate), magnesium oxide (e.g. magnesium oxide light), potassium bicarbonate ($KHCO_3$), sodium picosulphate (NaPIC), sodium saccharin, and orange flavour. Magnesium oxide "light" means, herein, magnesium oxide having an apparent volume such that 15 g occupies between 75 to 180 ml, e.g 15 g occupies a volume of 150 ml.

The known process for making PICOLAX™ may include the following steps. Granules of magnesium oxide and citric acid are produced by mixing the two reagents together—this is known as the "primary mix". In another stage, potassium bicarbonate, sodium picosulphate and water are mixed or blended to produce a wet "pre-mix", which is then dried. In a further stage, the flavour ingredients, orange flavour and sodium saccharin, are blended with the pre-mix and primary mix. The known process has several associated problems.

Firstly, the mixing processes may result in inhomogeneity problems in the final and intermediate products. In one aspect, the terms "inhomogeneity" and "lack of homogeneity" as used in this application refer to the lack of uniformity of content of the active substance—sodium picosulphate—in e.g. the final product. It also refers to the lack of homogeneity in the physical and morphological properties, such as the particle size (diameter) or particle size range or distribution, of the intermediate products and/or the final product granules. Intermediate product granules are, for example the primary mix granules or the pre-mix granules.

Homogeneity has been suspected to be at least one of the critical factors assuring the quality and performance of the final product, and it is believed that product homogeneity (and inhomogeneity) relates to the mixing processes used. Thus, in the first stage of the known process, disparities may occur in the granule size and distribution (i.e. inhomogeneity may arise) because of the low binding properties or agglomeration properties between citric acid and magnesium oxide particles (caused by e.g the difference in densities of the two materials). Further, magnesium oxide is left on the mixer bowl, blades etc. (rather than being mixed with the citric acid). Thus, in the known process, extra magnesium oxide ("overage") is included in the raw materials to compensate for losses during the blending process. The overage is typically over 10%. This leads to economic losses over longer periods and where larger quantities are produced. Additionally, longer processing times are entailed, and unhealthy amounts of dust may be produced during mixing.

In the premix stage, lack of homogeneity of the resulting granules may arise due to dissolution of some potassium bicarbonate in the granulation medium, water, and because of physical degradation (smashing) of the particles during mixing. This may have a detrimental effect on the final product. Further, long processing times, and multiple steps, are required to complete this stage of the process (which takes typically 15 to 24 hours).

Thus, there is a need for an improved manufacturing process.

SUMMARY OF THE INVENTION

The present applicants have developed a process which may alleviate some or all of the problems of the prior art process, and e.g. provide an improved product and/or a marked reduction in processing time.

There is provided therefore, according to an aspect of the present invention, a process for the preparation of a pharmaceutical composition comprising a homogeneous or substantially homogeneous mixture of citric acid, magnesium oxide, potassium bicarbonate and sodium picosuiphate and, optionally, saccharin sodium and/or orange flavour, comprising:

a) dry mixing citric acid and magnesium oxide;

b) applying (e.g. spraying) a solution of sodium picosulphate onto the potassium bicarbonate; and drying said sodium picosuiphate and potassium bicarbonate; and c) mixing at least a part of the product of step a) with at least a part of the product of step b) and, optionally, saccharin sodium and/or orange flavour.

In one example, the process includes a further step d) of mixing the product of step c) with further amount of a mixture formed by dry mixing citric acid and magnesium oxide [e.g. some or all of the remaining product of the process defined in step a)]; and/or a product formed by applying (e.g. spraying) a solution of sodium picosulphate on to potassium bicarbonate and drying the sodium picosuiphate and potassium bicarbonate [e.g. some or all of the remaining product of the process defined in step b)].

Thus, in one aspect there is provided a process for the preparation of a pharmaceutical composition, comprising a homogeneous or substantially homogeneous mixture of citric acid, magnesium oxide, potassium bicarbonate and sodium picosuiphate and, optionally, saccharin sodium and/or orange flavour, comprising:

a) dry mixing citric acid and magnesium oxide;

b) applying (e.g. spraying) a solution of sodium picosulphate onto the potassium bicarbonate; and drying said sodium picosuiphate and potassium bicarbonate;

c) mixing at least a part of the product of step a) with at least a part of the product of step b) and, optionally, saccharin sodium and/or orange flavour; and d) mixing the product of step c) with some or all of the remaining product of the process defined in step a); and/or some or all of the remaining product of the process defined in step b).

The product homogeneous or substantially homogeneous mixture of citric acid, magnesium oxide, potassium bicarbonate and sodium picosulphate and, optionally, saccharin sodium and/or orange flavour may be in the form of granules. The granule(s) may have a particle size (diameter) range or distribution of between about 100 and about 900 μm, e.g. between about 150 and 875 μm, e.g. between about 250 and about 850 μm. The pharmaceutical composition may be in the form of granules of e.g. a particle size (diameter) range or distribution of between about 100 and about 900 μm, e.g. between about 150 and 875 μm, e.g. between about 250 and about 850 μm.

It will be appreciated that herein the term diameter is not intended to mean that any of the particles and granules disclosed are spherical. As is clearly shown in the attached drawings the granules may be, for example, roughly spherical, in the form of elongated spheres (ellipsoidal) etc. Herein the term size (diameter) is intended to mean the shortest distance in a straight line passing from one side to the other through the centre point of the granule (e.g. sphere, rough sphere, elongated sphere, ellipsoid).

According to the present invention in a further aspect, there is provided a granule or granules or a pharmaceutical composition, comprising a homogeneous or substantially homogeneous mixture of citric acid, magnesium oxide, potassium bicarbonate and sodium picosulphate, and, optionally, saccharin sodium, and orange flavour. The pharmaceutical composition of the present invention may be used for clearance of the bowel prior to X-ray examination, endoscopy or surgery. The granule(s) may have a particle size (diameter) range or distribution of between about 100 and about 900 μm, e.g. between about 150 and 875 μm, e.g. between about 250 and about 850 μm.

Said granule(s) or pharmaceutical composition may be dispensed as sachets.

The uniformity of content of the active substance, sodium picosulphate, in the final product granule(s) or pharmaceutical composition may have a mean value of about 0.0559% and 0.068% by weight (9.0-11.0 mg/dose, based on a dose of 16.1 g PICOLAX™.).

According to the present invention in a further aspect, there is provided a pharmaceutical preparation or pharmaceutical composition comprising product granules of a homogeneous or substantially homogeneous mixture of a first composition comprising (first) granules of citric acid and magnesium oxide as described herein (e.g. comprising granules including citric acid and magnesium oxide, the granules comprising a layer of magnesium oxide coated on a core of citric acid); and a second composition comprising (second) granules of potassium bicarbonate and sodium picosulphate as described herein (e.g. comprising granules including sodium picosulphate and potassium bicarbonate, the granules comprising a layer of sodium picosulphate coated on a core of potassium bicarbonate); and, optionally, saccharin sodium and/or orange flavour. The product granule(s) may have a particle size (diameter) range between about 100 and about 900 μm. The product granule(s) may have a uniformity of content of sodium picosulphate of mean value between about 0.0559% and 0.068% by weight.

The process of the invention may include a separation (e.g. processing e.g. sieving) step or steps e.g. to obtain potassium bicarbonate of appropriate size and/or size distribution—e.g. a particle size (diameter) range of, for example, between about 100 and about 900 μm, e.g. between about 150 and 875 μm, e.g. between about 250 and about 850 μm—prior to applying (e.g. spraying). The process of the invention may include a separation (e.g. processing e.g. sieving) step or steps e.g. to obtain citric acid of appropriate size and/or size distribution—e.g. a particle size (diameter) range of, for example, between about 100 and about 900 μm, e.g. between about 150 and 875 μm, e.g. between about 250 and about 850 μm—prior to mixing with magnesium oxide.

The present invention also provides a process for the preparation of a pharmaceutical composition comprising a homogeneous or substantially homogeneous mixture of citric acid, magnesium oxide, potassium bicarbonate and sodium picosulphate and, optionally, saccharin sodium and/or orange flavour (and/or a process for the preparation of a composition comprising citric acid and magnesium oxide) comprising a step of dry mixing citric acid and magnesium oxide (e.g. magnesium oxide light), using a means for forming a homogeneous mixture of compounds with markedly different densities (such as a multi-dimension blender or three-dimensional blender). The means may mix using a three-dimensional motion (e.g. known as the Paul Schatz principle). The means may mix using a three-dimensional motion which combines a figure-of-eight movement with rotation, causing the substances within the mixer to move in a rhythmic, pulsating motion. The means may enhance the agglomeration process between citric acid and magnesium oxide. The means (e.g. multi-dimension blender or three-dimensional blender) may be closed during mixing, which may prevent dust or contamination. The means (e.g. multi-dimension blender or three-dimensional blender) may mix by an action whereby the mixing vessel is agitated or moved (e.g. spun) with a three dimensional motion, rather than by the use of a blade or paddle within the vessel (as in a conventional, planetary, mixer). The three dimensional motion may reduce particle damage (and inconsistent product size) associated with conventional mixing techniques—e.g. caused by frictional forces between the blade or paddle and mixing vessel side.

The citric acid may be loaded e.g. in a single batch into the means for forming a homogeneous or substantially homogeneous mixture of compounds with markedly different densities (such as a multi-dimension blender or three-dimensional blender), prior to addition of magnesium oxide. The magnesium oxide may be added in e.g. two to six, e.g. four, batches, with mixing between addition of each batch. The addition of MgO in small batches to the full amount of citric acid, and the mixing in between each addition of a batch of MgO, may enhance the agglomeration process between citric acid and magnesium oxide, and/or the homogeneity of the product mixture, and/or reduce the loss of MgO.

The process may include a separation (e.g. processing e.g. sieving) step or steps e.g. to obtain citric acid of appropriate size and/or size distributiuon—e.g. a particle size (diameter) range of, for example, between about 100 and about 900 μm, e.g. between about 150 and 875 μm, e.g. between about 250 and about 850 μm—prior to mixing with magnesium oxide. The process optionally includes one or more separation (e.g. sieving) steps e.g. to obtain product composition/granules of appropriate size (diameter) and/or size distribution.

The (product) composition/granules may have a particle size (diameter) and/or particle size (diameter) distribution which is compatible with the particle size or particle size distribution of the pre-mix or with the product of a step of applying (e.g. spraying) sodium picosulphate on potassium bicarbonate and drying.

According to a further aspect of the invention, granules (e.g. granules which are agglomerated particles) of citric acid and magnesium oxide are provided, having a particle size distribution range of between about 100 and about 900 μm, e.g. between about 150 and 875 μm, e.g. between about 250 and about 850 μm. The granules may have a particle size (diameter) distribution wherein more than 85%, for example more than 90%, for example more than 92% of the particles have a particle size (diameter) between about 100 and about 900 μm, e.g. between about 150 and 875 μm, e.g. between about 250 and about 850 μm. The granules may have a particle size (diameter) distribution wherein less than 5%, for example less than 2%, for example less than 1% of the particles have a particle size (diameter) greater than about 850 μm; and/or wherein less than 5%, for example less than 2%, for example less than 1% of the particles have a particle size (diameter) less than about 250 μm. The granules may have a particle size (diameter) distribution wherein less than 5%, for example less than 2%, for example less than 1% of the particles have a particle size (diameter) greater than about 875 μm; and/or wherein less than 5%, for example less than 2%, for example less than 1% of the particles have a particle size (diameter) less than about 150 μm. The granules may have a particle size (diameter) distribution wherein less than 5%, for example less than 2%, for example less than 1% of the particles have a particle size (diameter) greater than about 900 μm; and/or wherein less than 5%, for example less than 2%, for example less than 1% of the particles have a particle size (diameter) less than about 100 μm. The granules may have a particle size (diameter) range of, for example, between about 100 and about 900 μm, e.g. between about 150 and 875 μm, e.g. between about 250 and about 850 μm. The granules may have size or size distribution which is compatible with mixing with the product of a step of applying (e.g. spraying) a solution of sodium picosulphate on to potassium bicarbonate; and drying the sodium picosulphate and potassium bicarbonate (e.g. step b). The granules may include a layer of magnesium oxide coated on the citric acid.

According to a further aspect of the invention, there is provided a composition comprising granules including citric acid and magnesium oxide, the granules comprising a layer of magnesium oxide coated on a core of citric acid. The thickness of the layer of magnesium oxide may be between 2 and 15 μm, for example between 5 and 10 μm. The granules may be between 450 and 800 μm broad (e.g. 500 to 700 μm broad) at their broadest point [i.e. at the longest distance in a straight line passing from one side of the granule to the other through the centre point of the granule (e.g. sphere, rough sphere etc.).

In a further aspect, the present invention provides a process for the preparation of a pharmaceutical composition comprising a homogeneous or substantially homogeneous mixture of citric acid, magnesium oxide, potassium bicarbonate and sodium picosulphate and, optionally, saccharin sodium and/or orange flavour, (and/or a process for the preparation of a composition comprising potassium bicarbonate and sodium picosulphate,) comprising a step of applying (e.g. spraying) a solution of sodium picosulphate on to the potassium bicarbonate; and drying the sodium picosulphate and potassium bicarbonate.

The potassium bicarbonate may have a particle size (diameter) range of, for example, between about 100 and about 900 μm, e.g. between about 150 and 875 μm, e.g. between about 250 and about 850 μm. The process may include a separation (e.g. sieving) step or steps e.g. to obtain potassium bicarbonate of appropriate size and/or size distribution—e.g. a particle size (diameter) range of, for example, between about 100 and about 900 μm, e.g. between about 150 and 875 μm, e.g. between about 250 and about 850 μm.

The sodium picosulphate may be in aqueous solution. The ratio by weight of sodium picosulphate:water in the solution may be between 1:1 and 1:3, for example between 1:1.3 and 1:2.5, for example between about 1:1.5 and 1:2. The sodium picosulphate solution—e.g. aqueous solution—may be applied (e.g. sprayed) at a rate of 1 to 20 ml/min, preferably 10 to 12 ml/min.

In one example the sodium picosulphate is in aqueous solution. The solution—e.g. aqueous solution—may be applied (e.g. sprayed) onto the surface of e.g. granules or particles of potassium bicarbonate. The solution—e.g. aqueous solution—may be applied (e.g. sprayed) as e.g. microliquid drops.

The potassium bicarbonate may be preheated (e.g. prior to applying (e.g. spraying) the solution of sodium picosulphate on to the potassium bicarbonate) e.g. to a temperature of between 30° to 100° C., e.g. 30° C. to 70° C., e.g. 30° C. to 50° C. The sodium picosulphate and potassium bicarbonate may be dried at e.g. a temperature of between 30° to 100° C., e.g. 30° C. to 70° C., e.g. 30° C. to 50° C., for example 45° C. The drying may be by using [e.g. applying e.g. blowing] warm or hot air (e.g. at a temperature of between 30° to 100° C., e.g. 30° C. to 70° C., e.g. 30° C. to 50° C.). The drying may be during applying (e.g. spraying), and/or immediately or substantially immediately after applying (e.g. spraying). There may be one or more (e.g. 2, 3, 4 or more) applications (by e.g. spraying) of sodium picosulphate solution, the sodium picosulphate and potassium bicarbonate being dried during or immediately or substantially immediately after each (spray) application.

The applying (e.g. spraying) and drying may be performed e.g. in a tumble coating machine, or other coating machine (e.g. fluid bed coating machine) known to the skilled man.

The applying (e.g. spraying) and drying of sodium picosulphate and potassium bicarbonate may thus be finished in one step using the same coating machine instead of requiring two or more separate (mixing, drying) steps, and/or two or more separate machines.

The process may be auto-controlled. Thus, manual operations may be avoided, again allowing a reduction in the total process time.

The process may include a separation (e.g. sieving) step or steps to obtain product of appropriate size and/or size distribution—e.g. a particle size (diameter) range of, for example, between about 100 and about 900 μm, e.g. between about 150 and 875 μm, e.g. between about 250 and about 850 μm.

The (product) composition comprising potassium bicarbonate and sodium picosulphate may have a particle size (diameter) and/or particle size (diameter) distribution which is compatible with the particle size or particle size distribution of the primary mix or product of the step of dry mixing citric acid and magnesium oxide. The (product) composition comprising potassium bicarbonate and sodium picosulphate may have a particle size (diameter) distribution wherein more than 85%, for example more than 90%, for example more than 92% of the particles have a particle size (diameter) between about 100 and about 900 μm, e.g. between about 150 and 875 μm, e.g. between about 250 and about 850 μm. The (product) composition comprising potassium bicarbonate and sodium picosulphate may have a particle size (diameter) distribution wherein less than 5%, for example less than 2%, for example less than 1% of the particles have a particle size (diameter) greater than about 850 μm; and/or wherein less than 5%, for example less than 2%, for example less than 1% of the particles have a particle size (diameter) less than about 250 μm.

The (product) composition comprising potassium bicarbonate and sodium picosulphate may have a particle size (diameter) distribution wherein less than 5%, for example less than 2%, for example less than 1% of the particles have a particle size (diameter) greater than about 875 μm; and/or wherein less than 5%, for example less than 2%, for example less than 1% of the particles have a particle size (diameter) less than about 150 μm. The (product) composition comprising potassium bicarbonate and sodium picosulphate may have a particle size (diameter) distribution wherein less than 5%, for example less than 2%, for example less than 1% of the particles have a particle size (diameter) greater than about 900 μm; and/or wherein less than 5%, for example less than 2%, for example less than 1% of the particles have a particle size (diameter) less than about 100 μm. The (product) composition comprising potassium bicarbonate and sodium picosulphate may have a particle size (diameter) range or distribution of, for example, between about 100 and about 900 μm, e.g. between about 150 and 875 μm, e.g. between about 250 and about 850 μm.

The product or composition formed by applying (e.g. spraying) a solution of sodium picosulphate on to potassium bicarbonate and drying may be in the form of granules or particles, possessing improved homogeneity.

According to the present invention in a further aspect there is provided a composition comprising granules including sodium picosulphate and potassium bicarbonate, the granules comprising a layer of sodium picosulphate coated on a core of potassium bicarbonate. The granules may be e.g. substantially ellipsoidal [e.g. in the shape of an elongated sphere]. The granules may be substantially ellipsoidal in shape with the shortest distance in a straight line passing from one side of the granule to the other through the centre point of the granule being between 100 and 500 μm (e.g. 200 to 400 μm); and/or with the longest distance in a straight line passing from one side (end) of the granule to the other through the centre point of the granule being between 500 and 900 μm (e.g. 550 to 750 μm).

According to another aspect of the invention, pre-mix granules of sodium picosuiphate and potassium bicarbonate, having a particle size (diameter) range or distribution of between about 100 and about 900 μm, e.g. between about 150 and 875 μm, e.g. between about 250 and about 850 μm, are provided.

According to another aspect of the invention there is provided a granule or granules comprising a layer of sodium picosuiphate coated on potassium bicarbonate. The granules may have a particle size (diameter) distribution wherein more than 85%, for example more than 90%, for example more than 92% of the particles have a particle size (diameter) between about 100 and about 900 μm, e.g. between about 150 and 875 μm, e.g. between about 250 and about 850 μm. The granules may have a particle size (diameter) distribution wherein less than 5%, for example less than 2%, for example less than 1% of the particles have a particle size (diameter) greater than about 850 μm; and/or wherein less than 5%, for example less than 2%, for example less than 1% of the particles have a particle size (diameter) less than about 250 μm. The granules may have a particle size (diameter) distribution wherein less than 5%, for example less than 2%, for example less than 1% of the particles have a particle size (diameter) greater than about 875 μm; and/or wherein less than 5%, for example less than 2%, for example less than 1% of the particles have a particle size (diameter) less than about 150 μm. The granules may have a particle size (diameter) distribution wherein less than 5%, for example less than 2%, for example less than 1% of the particles have a particle size (diameter) greater than about 900 μm; and/or wherein less than 5%, for example less than 2%, for example less than 1% of the particles have a particle size (diameter) less than about 100 μm. The granules may have a particle size (diameter) range of, for example, between about 100 and about 900 μm, e.g. between about 150 and 875 μm, e.g. between about 250 and about 850 μm.

The pre-mix granules produced by methods of the present invention may possess a content of uniformity of sodium picosulphate (mg dose) which contributes to the homogeneity of final product. The present invention may provide, an intermediate composition or pre-mix, comprising potassium bicarbonate and sodium picosulphate, in the form of granules, which have a specified content of uniformity of sodium picosulphate (mg dose) which is consistent with that of the final product granule(s) or pharmacutical composition (see above) and a particle size (diameter) range of between about 100 and about 900 μm, e.g. between about 150 and 875 μm, e.g. between about 250 and about 850 μm.

It will be appreciated that herein process steps may be referred to as step a), b), c) etc. for clarity only; there is no express or implied requirement regarding ordering of steps. Thus, for example, the step a) process may be completed before, after, or substantially simultaneously with step b).

DETAILED DESCRIPTION OF THE INVENTION

The present invention will now be illustrated with reference to the following Examples.

The product PICOLAX™ is a physical mixture of six raw materials; these being citric acid (anhydrous), magnesium oxide, light, potassium bicarbonate (KHCO.sub.3), sodium picosulphate, saccharin sodium, and orange flavour.

In the first stage of the known process for making PICOLAX™ as discussed above, the "primary mix" comprising magnesium oxide and citric acid, is first produced. Extra magnesium oxide ("overage") is measured in as part of the feed to compensate for losses during the blending process. In the second stage, potassium bicarbonate, sodium picosulphate and water are mixed or blended to produce the "pre-mix". The pre-mix granulate is then dried. In the third stage, the flavour ingredients, orange flavour and sodium saccharin, are blended with the pre-mix and the primary mix.

According to the present invention in some aspects, the process also requires several stages.

The Primary Mix

In the prior art process, disparities were found to occur in the granule size and distribution, apparently due to the low binding properties or agglomeration properties between the citric acid and magnesium oxide particles. The prior art equipment employed, which was typically a tumble blender or planetary dry mixer, appeared to encourage separation of the two components, and loss of raw material in the form of fines, for example, of magnesium oxide. Using the known process, it is necessary to compensate on a regular basis for losses by adding extra magnesium oxide ("overage") in an amount of typically above 10%, which leads to economic losses over longer periods and larger quantities produced. Additionally, long processing times may be entailed, and unhealthy amounts of MgO dust may be produced during mixing. The prior art process may result in cleaning difficulties, and/or poor control of product granule/particle size and distribution.

A stage or step of present invention involves dry mixing of citric acid (CA) and magnesium oxide, to produce the "primary-mix". In contrast to the prior process, a better-agglomerated mixture may be obtained by mixing the citric acid and magnesium oxide using e.g. a multi-dimension blender or three-dimensional blender. The overage is significantly less. Three-dimensional blenders are known and may be obtained from e.g. Laval Lab Inc., of the US. The mixing vessel is moved using a three-dimensional motion (known as the Paul Schatz principle) which combines a figure-of-eight movement with rotation, causing the substances within the mixer to move in a rhythmic, pulsating motion. This motion may mix powders and granulates of differing weights, sizes and flow properties.

The multi-dimension blender utilizes strong physical force in the absence of a blade to mix materials, rather than a mechanical stirring agitator (as in a planetary dry mixer). This may reduce particle damage (and inconsistent product size) caused by frictional forces between the agitator blade or paddle and mixing vessel side. It also reduces dust from particle damage which is believed to affect the homogeneity of the final product, and/or sticking onto the mixing vessel internal wall. Further, cleaning is much easier because there is only the smooth interior surface to clean (no stirring agitator to clean).

The use of the multi-dimension blender or three-dimensional blender is accompanied by appropriate adjustments to the operational parameters, such as rotation speed, mixing time and material adding frequency.

The new process thus removes or significantly reduces the problems encountered in the prior process.

The Pre-Mix

In the second stage of the prior process, when producing the pre-mix, the sodium picosulphate was wet mixed with potassium bicarbonate. During wet mixing, a part of the potassium bicarbonate was dissolved, and part was smashed by the stirring agitator; these actions resulted in excess fine powder of potassium bicarbonate in the pre-mix after drying. A loss of product homogeneity was believed to result from this, because overly large particles or granules contain less sodium picosulphate, while overly fine particles or granules of the dried mixture contain too much sodium picosulphate; these extremes were believed to affect product homogeneity. The known process also required that the wet mixture was dried for a significant period. The known process also required several manual steps with the attendant risk of contamination to the product and increased operator safety concerns.

According to one or more aspects of the present invention, the process includes a step of applying (e.g. spraying) a solution of sodium picosulphate on to the potassium bicarbonate; and drying the sodium picosulphate and potassium bicarbonate.

This process for mixing may be thought of as akin to a coating process. The mixing/coating process may be carried out using an automatic tumble coating machine, e.g. with appropriate adjustments to the operational parameters made to control the coating level.

Thus, the solution (e.g. aqueous solution) of sodium picosulphate may be sprayed onto the potassium bicarbonate; and the said sodium picosulphate and potassium bicarbonate (i.e, the coated pre-mix granules) may be dried in the same equipment. This may lead to a significantly reduced production time; for example, the "pre-mix" of sodium picosulphate and potassium bicarbonate may be produced in about 3 hours [rather than about 15 to 24 hours using the prior process].

Further, the applicants found that there may be a significant reduction in inhomogeneity in the product granules, as follows. The sodium picosulphate solution may be sprayed very evenly onto the surface of the $KHCO_3$ granules and dried immediately after applying (e.g. spraying), and the amount of fine powder may be reduced. The granules are less likely to be reduced through, for example, smashing of particles/granules during a coating-type process. Further, because the coated granules may be dried instantly or substantially instantly e.g. with warm air, fine powder and dust may be significantly diminished.

Subsequently, the process of the invention may involve mixing of saccharin sodium, orange flavour, part of the primary mix and the pre-mix, with subsequent combination with the balance of the primary mix (and mixing) to provide the final homogeneous bulk product.

Thus, the disclosed invention may provide significant improvement in one, two, or more, steps in the mixing process. It may provide a more efficient process, of improved quality and reproducibility (e.g. with respect to uniformity of active substance). It may provide a method with reduced risk of contamination and/or loss of material, and/or with less manual operation. It may provide a method incurring significantly reduced process time.

The process according to the present invention may improve the homogeneity of the intermediate products of the primary mix and pre-mix mixing stages, as well as final product.

The present invention is now described with reference to the following examples.

Example 1

Method

Potassium Bicarbonate is sifted on sieves with screen size of 250 μm and 600 μm. Purified water is weighed out and Sodium Picosulphate is dissolved in the water to form a sodium picosulphate solution for the Pre-Mix stage. Sodium picosulphate solution and potassium bicarbonate are formed into a granulate by using a tumble coater (such coaters are well known in the art). Potassium Bicarbonate granules are filled into the coater, and a defined amount of Sodium Picosulphate solution is sprayed onto the surface of the granules during operation of the coater. The coated particles are then dried by warm air. After the coating process, pre-mix dried granules of combined Sodium Picosulphate and Potassium Bicarbonate are obtained.

Magnesium Oxide and Citric Acid are mixed to form primary mix granules by using a three-dimensional dry blender. Citric Acid is filled into the blender, and Magnesium Oxide, light is added. The materials in the blender are mixed by the usual operating method.

Orange flavour and Sodium Saccharin are blended together with Pre-mix and a known quantity of Primary mix to form a flavour blend. The flavour blend is then combined with the balance of Primary mix and mixed. The combined Final Blend powder is filled into foil sachets and packaged into cardboard boxes, using methods known in the art.

It is noted that the skilled man would readily understand the amount of reagent quantities etc. to be used (for ex., in a larger scale production process) depending on the amount of product desired.

Example 2

Formulations

The following formulations were made by the method described above. Each foil sachet contains the following ingredients.

| Reagent | Example 2a | Example 2b (16.1 g sachet) | Example 2c |
|---|---|---|---|
| Sodium picosulphate | 9 mg | 10 mg | 11 mg |
| Potassium hydrogencarbonate | 0.45 g | 0.5 g | 0.55 g |
| Magnesium oxide, light | 3.15 g | 3.5 g | 3.85 g |
| Citric acid | 10.8 g | 12 g | 13.2 |
| Saccharin sodium | 54 mg | 60 mg | 66 mg |
| Orange flavour* | 54 mg | 60 mg | 66 mg |

*natural spray dried orange flavour which includes butylated hydroxyanisole

Example 3

SEM Pictures and EDAX Analysis Results

The SEM and EDAX pictures were taken at the Electron Microscope Lab at the Instrumentation Analysis and Research Centre, Sun Yat-sen University, China.

SEM pictures and EDAX analysis of a Primary Mix granule of citric acid and magnesium oxide, made by the method of Example 1, show that the element MgO is found on the outer shell of the granule. The core of the granule has very little element MgO (the trace amount being due to contamination during cutting the sample in the preparation process for EDAX), while the shell includes a large quantity of MgO. The Sum Spectrum shows the sum of element MgO on the surface of the granule (the cut section and the shell).

The granule has a crystal core of Citric Acid and a white shell of MgO. The layer thickness of the MgO shell may be calculated from the black and white photo (e.g. using a ruler) to be 5-10 μm.

SEM and EDAX of a Pre Mix granule of sodium picosulphate and potassium bicarbonate, also made by the method of Example 1, show that the element S (i.e. Sodium Picosulfate) is clearly detected on the shell and the element K (i.e. Potassium Bicarbonate) is clearly detected on the core. Most of element S occupies the shell; the little quantity of element S on the cut section plane is contamination caused by the cutting operation in the sample preparation process for EDAX. The cut section plane (the core of the granule) has more of element K than the shell. The shell includes both element K and S, indicating that the layer of Sodium Picosulfate is very thin (because its quantity is very low—only 2% according to this formulation of Pre-Mix). The granule has a (crystal) core of Potassium bicarbonate and a (white) shell of Sodium Picosulfate. The granule may be described as substantially ellipsoidal.

The invention claimed is:

1. A pharmaceutical composition comprising:
   (a) magnesium oxide coated granules which have a layer of magnesium oxide coated on a core of citric acid; and
   (b) sodium picosulphate coated granules having a spray-coated layer of sodium picosulphate coating a potassium bicarbonate core.

2. The pharmaceutical composition according to claim 1 wherein the thickness of the layer of magnesium oxide is 2 to 15 μm.

3. The pharmaceutical composition according to claim 1 wherein the thickness of the layer of magnesium oxide is 5 to 10 μm.

4. The pharmaceutical composition according to claim 1 wherein the magnesium oxide coated granules are between 450 and 800 μm broad at their broadest point.

5. The pharmaceutical composition according to claim 1 wherein the magnesium oxide coated granules have a particle size between about 100 μm and 900 μm.

6. The pharmaceutical composition according to claim 1 wherein more than 85% of the magnesium oxide coated granules have a size between about 100 μm and about 900 μm.

7. The pharmaceutical composition according to claim 1 wherein less than 5% of the magnesium oxide coated granules have a size greater than about 900 μm; or wherein less than 5% of the magnesium oxide coated granules have a size less than about 100 μm.

8. The pharmaceutical composition according to claim 1, wherein the magnesium oxide and citric acid form magnesium citrate in solution.

9. The pharmaceutical composition according to claim 1, additionally comprising saccharin sodium.

10. The pharmaceutical composition according to claim 1, additionally comprising orange flavoring.

11. The pharmaceutical composition according to claim 1, additionally comprising saccharin sodium and orange flavoring.

* * * * *